US007879604B2

(12) United States Patent
Seyedin et al.

(10) Patent No.: US 7,879,604 B2
(45) Date of Patent: Feb. 1, 2011

(54) INTERVERTEBRAL DISK REPAIR, METHODS AND DEVICES THEREFOR

(75) Inventors: Mitchell S. Seyedin, Monte Sereno, CA (US); Robert Spiro, Half Moon Bay, CA (US); H. Davis Adkisson, IV, St. Louis, MO (US)

(73) Assignee: Isto Technoliges, Inc., St. Louis, MI (US)

( * ) Notice: Subject to any disclaimer, the term of this patent is extended or adjusted under 35 U.S.C. 154(b) by 134 days.

(21) Appl. No.: 11/063,183

(22) Filed: Feb. 22, 2005

(65) Prior Publication Data

US 2005/0196387 A1 Sep. 8, 2005

Related U.S. Application Data

(60) Provisional application No. 60/546,619, filed on Feb. 20, 2004.

(51) Int. Cl.
C12N 5/00 (2006.01)
A61F 2/00 (2006.01)

(52) U.S. Cl. ................ 435/325; 435/366; 435/363; 424/423; 424/400

(58) Field of Classification Search .............. None
See application file for complete search history.

(56) References Cited

U.S. PATENT DOCUMENTS

| | | | |
|---|---|---|---|
| 4,965,203 A | 10/1990 | Silbering et al. | |
| 5,047,055 A | 9/1991 | Bao et al. | |
| 5,192,326 A | 3/1993 | Bao et al. | |
| 5,326,357 A | 7/1994 | Kandel | |
| 5,516,532 A * | 5/1996 | Atala et al. | 424/548 |
| 5,674,295 A | 10/1997 | Ray et al. | |
| RE35,694 E | 12/1997 | Seyedin et al. | |
| 5,723,331 A * | 3/1998 | Tubo et al. | 435/366 |
| 5,824,093 A | 10/1998 | Ray et al. | |
| 5,834,420 A | 11/1998 | Laub et al. | |
| 5,879,359 A | 3/1999 | Dorigatti et al. | |
| 6,022,376 A | 2/2000 | Assell et al. | |
| 6,027,744 A | 2/2000 | Vacanti et al. | |
| 6,063,061 A | 5/2000 | Wallace et al. | |
| 6,077,989 A | 6/2000 | Kandel et al. | |
| 6,110,210 A | 8/2000 | Norton et al. | |
| 6,132,465 A | 10/2000 | Ray et al. | |
| 6,206,921 B1 | 3/2001 | Guagliano et al. | |
| 6,224,630 B1 | 5/2001 | Bao et al. | |
| 6,235,316 B1 | 5/2001 | Adkisson | |
| 6,306,169 B1 * | 10/2001 | Lee et al. | 623/11.11 |
| 6,340,369 B1 | 1/2002 | Ferree | |
| 6,352,557 B1 | 3/2002 | Ferree | |
| 6,371,990 B1 | 4/2002 | Ferree | |
| 6,428,576 B1 | 8/2002 | Haldimann | |
| 6,454,804 B1 | 9/2002 | Ferree | |
| 6,645,316 B1 | 11/2003 | Brouwer et al. | |
| 6,645,764 B1 | 11/2003 | Adkisson | |
| 6,648,920 B2 | 11/2003 | Ferree | |
| 6,685,695 B2 | 2/2004 | Ferree | |
| 6,723,335 B1 | 4/2004 | Moehlenbruck et al. | |
| 6,793,677 B2 | 9/2004 | Ferree | |
| 6,921,532 B1 | 7/2005 | Austin et al. | |
| 2001/0051834 A1 | 12/2001 | Frondoza et al. | |
| 2002/0103542 A1 | 8/2002 | Bilbo | |

FOREIGN PATENT DOCUMENTS

| | | |
|---|---|---|
| WO | 9904720 A1 | 2/1999 |
| WO | 0240070 A2 | 5/2002 |
| WO | 0240070 A3 | 5/2002 |

OTHER PUBLICATIONS

Adkisson et al., "In Vitro Generation of Scaffold Independent Neocartilage," Clin. Orthop. Rel. Res., 2001, pp. S280-S294, vol. 391S.

Chang et al., "Cartilage-Derived Morphogenetic Proteins," J. Biol. Chem., 1994, pp. 28227-28234, vol. 269.

Ehlers et al., "Effects of Hyaluronic Acid on the Morphology and Proliferation of Human Chondrocytes in Primary Cell Culture," Ann. Anat., 2000, pp. 13-17, vol. 183.

Feder et al., Tissue Engineering in Musculoskeletal Clinical Practice, American Academy of Orthopaedic Surgeons, 2004.

Ganey et al., "Disc Chondrocyte Transplantation in a Canine Model: A Treatment for Degenerated or Damaged Intervertebral Disc," Spine, 2003, pp. 2609-2620, vol. 28.

Garfin et al., "New Technologies in Spine: Kyphoplasty and Vertebroplasty for the Treatment of Painful Osteoporotic Compression Fractures," Spine, 2001, pp. 1511-1515, vol. 26.

Halm et al., "Comparing Ease of Intraosseous Needle Placement: Jamshidi Versus Cook.," Am. J. Emerg. Med., 1998, pp. 420-422, vol. 16.

Han et al., "The Value of Jamshidi Core Needle Bone Biopsy in Predicting Postoperative Osteomyelitis in Grade IV Pressure Ulcer Patients," Plast. Reconstr. Surg., 2002, pp. 118-122, vol. 110.

Kato et al., "Sulfated Proteoglycan Synthesis by Confluent Cultures of Rabbit Costal Chondrocytes Grown in the Presence of Fibroblast Growth Factor," J. Cell Biol., 1985, pp. 477-485, vol. 100.

Reddi, "Cartilage Morphogenetic Proteins: Role in Joint Development, Homoeostasis, and Regeneration," Ann. Rheum. Dis., 2003, pp. ii73-ii78, vol. 62.

(Continued)

Primary Examiner—Lora E Barnhart
(74) Attorney, Agent, or Firm—Polsinelli Shughart PC

(57) ABSTRACT

The present application discloses compositions, methods and devices for treatment of a degenerative intervertebral disc. A composition can comprise chondrocytes expressing type II collagen. These chondrocytes can be obtained from human cadavers up to about two weeks following death, and can be grown in vitro. The compositions can further comprise one or more biocompatible molecules. Treatment of a degenerative disc can comprise injecting or implanting a composition comprising the chondrocytes into a degenerative disc.

7 Claims, 9 Drawing Sheets

OTHER PUBLICATIONS

Mathis et al., "Percutaneous Vertebroplasty: Technical Considerations," J. Vasc. Interv. Radiol., 2003, pp. 953-960, vol. 14.

Ganey, et al., Disc Chondrocyte Transplantation in a Canine Model: A Treatment for Degenerated or Damaged Intervertebral Disc, Spine, 2003, pp. 2609-2620, vol. 28, No. 23.

Gruber, et al., Autologous Intervertebral Disc Cell Implantation, Spine, 2002, pp. 1626-1633, vol. 27, No. 15.

Kim, et al., A Disc Mimetic Bioreactor Culture System For Mesenchymal Stem Cells, 53rd Annual Meeting Program Book, Orthopaedic Research Society, Feb. 11-14, 2007, Poster 1078.

Poiraudeau, et al., Phenotypic Characteristics of Rabbit Intervertebral Disc Cells, Spine, 1999, pp. 837-844, vol. 24, No. 9.

Sandell, et al., Tissue Engineering in Musculoskeletal Clinical Practice, American Academy of Orthopaedic Surgeons, 2003, pp. 218-226, Chapter 22.

Sato, et al., An Experimental Study of the Regeneration of the Intervertebral Disc With an Allograft of Cultured Annulus Fibrosus Cells Using a Tissue-Engineering Method, Spine, 2003, pp. 548-553, vol. 28, No. 6.

Kim, et al., Juvenile Chondrocytes May Facilitate Disc Repair, 53rd Annual Meeting Program Book, Orthopaedic Research Society, Feb. 11-14, 2007, Poster 1091.

Sakai et al, Transplantation of mesenchymal stem cells embedded in Atelocollagen® gel to the intervertebral disc: a potential therapeutic model for disc degeneration, Biomaterials, 2003, pp. 3531-3541, vol. 24.

Sato et al, An Experimental Study of the Regeneration of the Intervertebral Disc With an Allograft of Cultured Annulus Fibrosus Cells Using a Tissue-Engineering Method, Spine, 2003, pp. 548-553, vol. 28, No. 6.

Nomura et al, Nucleus Pulposus Allograft Retards Intervertebral Disc Degeneration, Clinical Orthopaedics and Releated Research, 2001, pp. 94-101, No. 389.

Brisby et al, Cell therapy for disc degeneration-potentials and pitfalls, Orthop CLin N. Am, 2004, pp. 85-93, vol. 35.

Zhao et al, The cell biology of intervertebral disc aging and degeneration, Ageing Research Reviews, 2007, pp. 247-261, vol. 6.

Benya et al., Dedifferentiated Chondrocytes Reexpress the Differentiated Collagen Phenotype When Cultured in Agarose Gels, Cell, 1982, pp. 215-224, vol. 30.

Chelberg et al., Identification of heterogeneous cell populations in normal human intervertebral disc, J. Anal., 1995, pp. 43-53, vol. 186.

Delmage et al., The Selective Suppression of Immunogenicity by Hyaluronic Acid, J. Clin. Lab. Sci., 1986, pp. 303-310, vol. 16, No. 4.

Eyre, David, Collagen of articular cartilage, Arthritis Res., 2002, pp. 30-35, vol. 4.

Haufe et al., Intradiscal Injection of Hematopoietic Stem Cells in an Attempt to Rejuvenate the Intervertebral Discs, Stem Cells and Development, 2006, pp. 136-137, vol. 15.

Hunter et al., The Three-dimensional architecture of the notochordal nucleus pulposus: novel observations on cell structures in the canine intervertebral disc, J. Anat., 2003, pp. 279-291, vol. 202.

Kuettner et al, Synthesis of Cartilage Matrix by Mammalian Chondrocytes In Vitro. II. Maintenance of Collagen and Proteoglycan Phenotype, J. Cell Biol., 1982, pp. 751-757, vol. 93.

Lee et al., A phenotypic comparison of intervertebral disc and articular cartilage cells in the rat, Eur. Spine J., 2007, pp. 2174-2185, vol. 16.

Mochida, J, New strategies for disc repair: novel preclinical trials, J. Orthopaedic Science, 2005, pp. 112-118, vol. 10.

Okuma et al., Reinsertion of Stimulated Nucleus Pulposus Cells Retards Intervertebral Disc Degeneration: An In Vitro and In Vivo Experimental Study, J. Orthopaedic Res., 2000, pp. 988-997, vol. 18.

Steck et al., Induction of Intervertebral Disc-Like Cells From Adult Mesenchymal Stem Cells, Stem Cells, 2005, pp. 403-411, vol. 23.

Thomas et al., Cartilage collagens: strategies for the study of their organisation and expression in the extracellular matrix, Annals of the Rheumatic Diseases, 1994, pp. 488-496, vol. 53.

Urban et al., Intervertebral Disc, in Extracellular Matrix Tissue Function, 1996, Comper WD, ed, vol. 1, pp. 203-233.

Wu et al., Type VI collagen of the intervertebral disc, Biochem J., 1987, pp. 373-381, vol. 248.

Hohaus et al., Cell transplantation in lumbar spine disc degeneration disease, Eur. Spine J., 2008, pp. S492-S503, vol. 17, Suppl. 4.

Office Action dated May 19, 2009, U.S. Appl. No. 11/458,278, Intervertebral Disc Repair, Methods and Devices Therefor, 21 pages.

Gorensek et al., "Nucleus Pulposus Repair with Cultured Autologous Elastic Cartilage Derived Chondrocytes," Cell. Mol. Biol. Lett., 2004, pp. 363-373, vol. 9.

Mwale et al., "Distinction Between the Extracellular Matrix of the Nucleus Pulposes and Hyaline Cartilage: A Requisite for Tissue Engineering or Intervertebral Disc," Euro. Cell. Mat., 2004, pp. 58-64, vol. 8.

Rousou, J. et al., "Randomized clinical trial of fibrin sealant in patients undergoing resternotomy or reoperation after cardiac operations," J Thorac Cardiovasc Surg 1989; 97:194-203.

* cited by examiner

Juvenile cartilage graft in fibrin gel

Disc space 12 weeks after chondrocyte injection with fibrin

INTERVERTEBRAL DISK REPAIR, METHODS AND DEVICES THEREFOR

CROSS-REFERENCE TO RELATED APPLICATIONS

This application claims priority from U.S. Provisional application No. 60/546,619 filed Feb. 20, 2004, which is incorporated herein by reference in its entirety.

STATEMENT REGARDING FEDERALLY SPONSORED RESEARCH OR DEVELOPMENT

Not Applicable.

BACKGROUND OF THE INVENTION

Intervertebral disc degeneration is a leading cause of pain and disability in the adult population. Approximately 80% of the population experience at least a single episode of significant back pain in their lifetimes. For many individuals, spinal disorders become a lifelong affliction. The morbidity associated with disc degeneration and its spectrum of associated spinal disorders is responsible for significant health care, economic and social costs. Furthermore, changes in disc morphology, such as disc compression associated with aging, can lead to unwanted changes in height or posture. Current treatments for repairing or ameliorating disc degeneration, such as spinal fusion, can be expensive, painful, or lengthy. Alternative treatments are, therefore, needed.

BRIEF SUMMARY OF THE INVENTION

In view of the need for disc degeneration treatments, the present inventors have devised compositions, methods and devices for repair, replacement and/or supplementation of an intervertebral disc which involve implantation or injection of chondrocytes into a degenerative disc, as well as compositions and methods for providing chondrocytes to a treatment provider.

Some embodiments of the present teachings include methods of repairing a degenerative intervertebral disc in a human patient in need of treatment. In these embodiments, a method can comprise implanting, into the intervertebral disc, chondrocytes obtained from a cadaver. The cadaver chondrocytes can be from any cartilaginous tissue of the cadaver, provided the chondrocytes express type II collagen. Furthermore, the chondrocytes expressing type II collagen can be chondrocytes expressing high molecular weight sulfated proteoglycan (HSPG). The chondrocytes can be, for example, hyaline cartilage chondrocytes. In various configurations, the chondrocytes can be chondrocytes from one or more intervertebral discs, or the chondrocytes can be non-intervertebral disc chondrocytes. Chondrocytes from an intervertebral disc can be chondrocytes from the annulus of a disc, chondrocytes from the nucleus pulposus of a disc, or a combination thereof. Non-limiting examples of non-intervertebral disc tissue which can be sources of chondrocytes include cartilage of the nose, ears, trachea and larynx, as well as articular cartilage, costal cartilage, cartilage of an epiphyseal plate, and combinations thereof. In various aspects of the present teachings, the chondrocytes can be extracted from a cadaver at any time following death while the chondrocytes remain viable. In various configurations, chondrocytes can be extracted from a cadaver up to about fourteen days following death. Chondrocytes can be removed from a cadaver from about one hour following death to about fourteen days following death, from greater than 24 hours following death to about thirteen days following death, from about two days following death to about twelve days following death, from about three days following death to about twelve days following death, or from about four days following death to about ten days following death.

In some embodiments, chondrocytes of the present teachings can be chondrocytes extracted from a cadaver of any chronological age at time of death. In various configurations, chondrocytes can be extracted from a cadaver which is no older than about 40 years of age at time of death, no older than about 30 years of age at time of death, no older than about 20 years of age at time of death, or no older than about 10 years of age at time of death. A donor cadaver need not be a familial member of a recipient, or be otherwise matched immunologically.

In various embodiments, chondrocytes which are extracted from a cadaver can be grown in vitro prior to their implantation or injection into a recipient patient or purveyance to a treatment provider. Growth of chondrocytes in vitro can be used, for example, to increase the number of chondrocytes available for implantation or injection. In non-limiting example, chondrocyte numbers can be increased about two fold or greater, about ten fold or greater, or about twenty fold or greater. In various configurations, growing chondrocytes in vitro can comprise placing one or more cartilage tissue pieces removed from a cadaver into a tissue culture or cell culture medium which comprises nutrients, buffers, salts, proteins, vitamins and/or growth factors which promote chondrocyte growth, and incubating the chondrocytes. In certain configurations, tissue comprising chondrocytes expressing type II collagen can be dissociated into single cells or small groups of cells prior to, or in conjunction with, their introduction into a culture medium. In addition, in some aspects, in vitro culture of chondrocytes expressing type II collagen can further comprise removing non-chondrocyte cells from a cell- or tissue-culture.

In various embodiments of the present teachings, chondrocytes expressing type II collagen can be comprised by a composition which can be implanted or injected into an intervertebral disc of a patient in need of treatment. Accordingly, in certain embodiments, the present teachings also include compositions comprising cadaver chondrocytes expressing type II collagen for use in implantation or injection into a degenerative intervertebral disc of a patient in need of treatment. In some configurations of these embodiments, the chondrocytes of these compositions can comprise chondrocytes expressing high molecular weight sulfated proteoglycan. In some configurations, a composition comprising chondrocytes expressing type II collagen can further comprise at least one biocompatible molecule. Non-limiting examples of biocompatible molecules which can be comprised by a composition of the present teachings include fibrinogen, fibrin, thrombin, type I collagen, type II collagen, type III collagen, fibronectin, laminin, hyaluronic acid (HA), hydrogel, pegylated hydrogel, chitosan, and combinations thereof.

In various embodiments, the present teachings include methods of forming a composition comprising cadaver chondrocytes. A composition formed by these methods can further comprise one or more biocompatible molecules such as those described supra. Accordingly, methods of these embodiments can comprise contacting cadaver chondrocytes expressing type II collagen with one or more biocompatible molecules, such as, for example, fibrinogen, fibrin, thrombin, type I collagen, type II collagen, type III collagen, fibronectin, laminin, hyaluronic acid, hydrogel, pegylated hydrogel, chitosan and combinations thereof. The cadaver chondrocytes expressing type II collagen can be, in some configurations, chondrocytes which also express high molecular weight sulfated proteoglycan. In certain aspects, the chondrocytes can be incubated in vitro in a culture medium prior to the contacting with one or more biocompatible molecules.

In various embodiments, the present teachings include methods of forming a composition comprising cadaver tissue comprising chondrocytes. A composition formed by these methods can further comprise one or more biocompatible molecules such as those described supra. Accordingly, methods of these embodiments can comprise contacting cadaver tissue comprising chondrocytes expressing type II collagen with one or more biocompatible molecules, such as, for example, fibrinogen, fibrin, thrombin, type I collagen, type II collagen, type III collagen, fibronectin, laminin, hyaluronic acid, hydrogel, pegylated hydrogel, chitosan and combinations thereof. The cadaver chondrocytes expressing type II collagen can be, in some configurations of these embodiments, chondrocytes which also express high molecular weight sulfated proteoglycan. In certain aspects of these embodiments, cadaver tissue comprising chondrocytes expressing type II collagen can be incubated in vitro in a culture medium prior to the contacting with one or more biocompatible molecules.

In various aspects of the present teachings, a composition comprising both cadaver chondrocytes expressing type II collagen and one or more biocompatible molecules can be implanted or injected into a degenerative intervertebral disc in a patient in need of treatment. In various aspects, implantation or injection of a composition into a disc can comprise implantation or injection of the composition into the annulus of the disc, implantation or injection of the composition into the nucleus pulposus of the disc, implantation or injection of the composition into one or both endplates of the disc, or a combination thereof. In some configurations, an aperture can be formed in an annulus of a degenerative disc, and a composition can be introduced into the disc through the aperture. In some configurations, surgical techniques such as vertebroplasty and kyphoplasty (Garfin, S. R., et al., Spine 26: 1511-1515, 2001) can be adapted or modified for introducing chondrocytes into a degenerative disc of a patient.

In various embodiments, the present teachings include an apparatus configured for injection of chondrocytes expressing type II collagen to an intervertebral disc of a patient in need of treatment. An apparatus configured for injection of chondrocytes expressing type II collagen into an intervertebral disc can comprise chondrocytes expressing type II collagen. Chondrocytes of these embodiments can comprise chondrocytes expressing high molecular weight sulfated proteoglycan. In various configurations, the apparatus can comprise a composition which comprises the chondrocytes and at least one biocompatible molecule, such as, for example, a biocompatible molecule described supra. In certain embodiments, the chondrocytes expressing type II collagen comprised by the apparatus can be cadaver chondrocytes. The cadaver chondrocytes in these embodiments can be intervertebral disc chondrocytes, or non-intervertebral disc chondrocytes, such as those described supra. In some configurations of these embodiments, the chondrocytes can be comprised by cadaver tissue. An apparatus of the present teachings can further comprise, in some configurations, a syringe, a double syringe, a hollow tube, such as a hollow needle (for example, a Jamshidi needle), a cannula, a catheter, a trocar, a stylet, an obturator, or other instruments, needles or probes for cell or tissue injection, injection, or transfer known to skilled artisans. In certain configurations, the apparatus can be configured for injection of chondrocytes expressing type II collagen into a nucleus pulposus of an intervertebral disc, an annulus of an intervertebral disc, an endplate of an intervertebral disc or a combination thereof.

In various embodiments of the present teachings, methods are provided for purveying to a treatment provider chondrocytes for repairing a degenerative intervertebral disc in a patient in need thereof. In various aspects, a method of these embodiments can comprise growing cadaver chondrocytes expressing type II collagen in vitro, and delivering the chondrocytes expressing type II collagen to the treatment provider. Chondrocytes expressing type II collagen of these embodiments can be, in some configurations, chondrocytes which also express high molecular weight sulfated proteoglycan. Methods of these embodiments can further comprise obtaining chondrocytes expressing type II collagen from a cadaver. In these embodiments, the cadaver chondrocytes expressing type II collagen can be obtained at various time intervals following death of the donor as described supra. Furthermore, a donor cadaver of chondrocytes expressing type II collagen can be of an age at time of death as described supra. The chondrocytes of these embodiments can be chondrocytes of tissue sources such as those described supra.

In some configurations of these methods, the chondrocytes expressing type II collagen can be purveyed to a treatment provider along with one or more biocompatible molecules, such as those described supra. In some configurations, a composition comprising the chondrocytes and one or more biocompatible molecules can be purveyed to a treatment provider. In other configurations, the chondrocytes and the one or more biocompatible molecules can be purveyed separately to a treatment provider (either simultaneously or at different times), and the treatment provider can form a composition comprising the chondrocytes and the one or more biocompatible molecules prior to, or in conjunction with, implanting the composition in a patient in need thereof.

In various embodiments, the teachings of the present application also disclose use of cadaver chondrocytes expressing type II collagen for the production of a composition for repairing a degenerative intervertebral disc in a patient in need thereof. In some configurations of these embodiments, the chondrocytes can also express high molecular weight sulfated proteoglycan. In certain configurations of these embodiments, the chondrocytes can be cadaver chondrocytes which are grown in vitro, as described supra. A composition of these embodiments can comprise a composition comprising cadaver chondrocytes expressing type II collagen and one or more biocompatible molecules such as those described supra. In addition, the time interval following death at which the chondrocytes can be removed from a donor can be a time interval as described supra, and the age of a donor cadaver at time of death can be an age as described supra. In some aspects of these embodiments, the chondrocytes can include chondrocytes removed from an annulus, chondrocytes removed from a nucleus pulposus, chondrocytes removed from an endplate of an intervertebral disc of a donor cadaver, or a combination thereof. In some other aspects of these embodiments, the chondrocytes can be chondrocytes removed from other cartilaginous, non-intervertebral disc tissue of a cadaver, such as, for example, hyaline cartilage from the nose, ears, trachea or larynx, as well as articular cartilage, costal cartilage, cartilage of an epiphyseal plate, or combinations thereof.

BRIEF DESCRIPTION OF THE DRAWINGS

These and other features, aspects, and advantages of the present invention will become better understood with regard to the following description, appended claims and accompanying figures where:

DETAILED DESCRIPTION OF THE INVENTION

Figure 1:
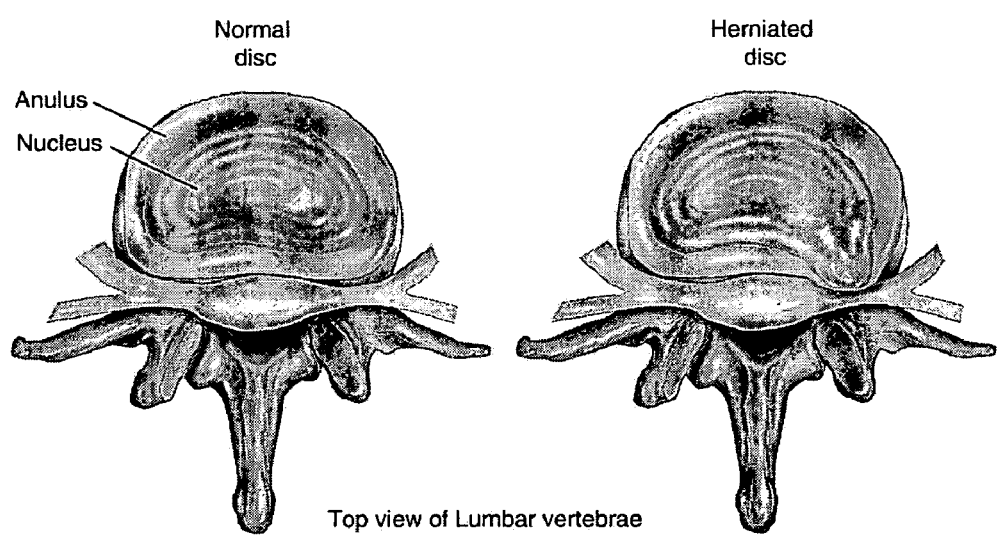
FIG. 1 illustrates a normal intervertebral disc (left) and a herniated disc (right).
Figure 2:
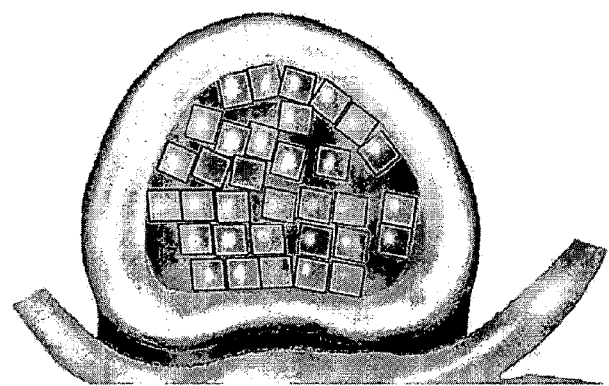
FIG. 2 illustrates freshly isolated, juvenile cartilage tissue that has been dissected to small cubes and implanted into a damaged nucleus pulposus region of an intervertebral disc in a composition which can also comprise a biocompatible molecule.
Figure 3:
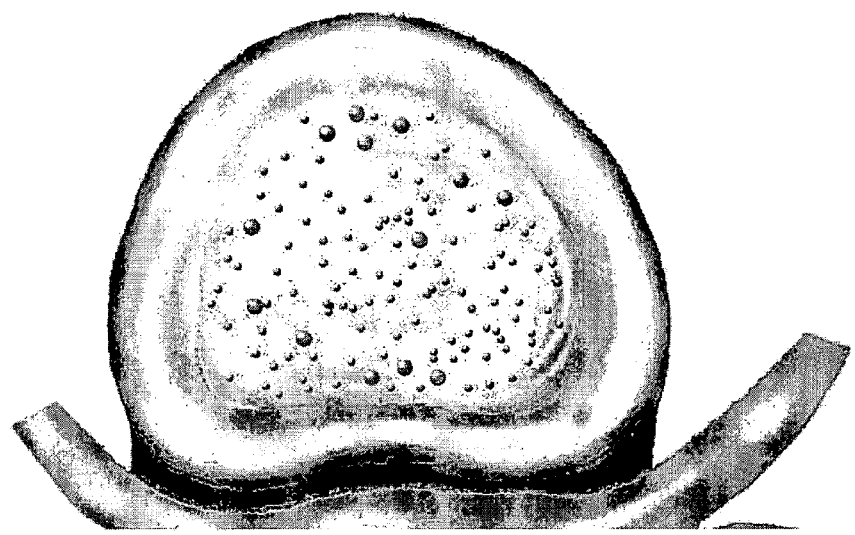
FIG. 3 illustrates isolated juvenile chondrocytes, freshly isolated or harvested from expanded in vitro cultures which can be implanted into the nucleus pulposus region of an intervertebral disc in a composition which can also comprise a biocompatible molecule.

The present teachings describe compositions, methods and devices for repair, replacement and/or supplementation of a degenerative intervertebral disc. These methods can involve implantation or injection of chondrocytes into a degenerative disc. In addition, the present teachings also describe methods for providing chondrocytes to a treatment provider.

As used herein, the terms "degenerative intervertebral disc" and "degenerative disc" refer to an intervertebral disc exhibiting disease symptoms, abnormalities or malformations, including but not limited to herniations, disruptions, traumatic injuries, and morphological changes associated with or attributed to aging. Indications of a degenerative intervertebral disc can include, but are not limited to, brittleness of an annulus, tearing of an annulus, and shrinking of a nucleus pulposus.

In various embodiments, the present teaching include methods of repairing a degenerative disc in a human patient in need of treatment. Methods of these embodiments can comprise implanting or injecting into the intervertebral disc a composition comprising cadaver chondrocytes. As used herein, the term "cadaver chondrocytes" refers to viable chondrocytes originally comprised by a human cadaver, as well as clonal descendants of such chondrocytes, such as chondrocytes grown in vitro. Cadaver chondrocytes for use in the various aspects of the present teachings can be obtained from tissues comprising chondrocytes from a cadaver, such as cartilage tissue. Such tissues can be dissected from a cadaver using standard dissection methods well known to skilled artisans. The cartilage tissue utilized in the present teachings can comprise hyaline cartilage, such as cartilage of the nose, ears, trachea and larynx, articular cartilage, costal cartilage, cartilage of an epiphyseal plate, and combinations thereof. In various aspects, the cartilage tissue or chondrocytes can be intervertebral disc cartilage or chondrocytes, or can be cartilage or chondrocytes originating from cartilaginous tissues other than intervertebral disc tissue (herein referred to as "non-intervertebral disc chondrocytes"). Viable chondrocytes can be comprised by cartilaginous tissues in a donor cadaver for up to about two weeks after death of the donor. Accordingly, in some configurations, the time interval from the time of death of a donor (as determined, for example, by a physician or a coroner) to the time of dissection of cartilage tissue from the donor can be any time from about immediately following a pronouncement of death, to about two weeks following death, such as, without limitation, about one hour, greater than 24 hours, about two days, about three days, about four days, about five days, about six days, about seven days, about eight days, about nine days about ten days, about eleven days, about twelve days, about thirteen days, or about fourteen days after death. In addition, a donor cadaver can be of any chronological age at time of death. For example, a donor cadaver can be, at time of death, ten years old or younger, twenty years old or younger, thirty years old or younger, or forty years old or younger. A donor cadaver need not be a familial member of a recipient, or be otherwise matched immunologically. Without being limited by theory, it is believed that intervertebral cartilage comprises an "immunologically privileged" tissue, so that chondrocytes transplanted to an intervertebral disk are not subject to rejection by the recipient's immune system.

Cartilage tissue can be removed from a cadaver using any surgical or dissecting techniques and tools known to skilled artisans. Following cartilage removal from a cadaver, the cartilage tissue can be minced, dissociated into single cells or small groups of cells, and/or placed into tissue or cell culture using standard techniques and apparatuses well known to skilled artisans, such as techniques and apparatuses described in the these references. Non-limiting descriptions of methods of cartilage and chondrocyte removal and culture can be found in references such as, for example, Feder, J. et al. in: Tissue Engineering in Musculoskeletal Clinical Practice. American Academy of Orthopaedic Surgeons, 2004; Adkisson, H. D. et al., Clin. Orthop. 391S:S280-S294, 2001; and U.S. Pat. Nos. 6,235,316 and 6,645,316 to Adkisson.

Cadaver chondrocytes used in the various embodiments of the present teachings are all cadaver chondrocytes which express type II collagen. In addition, in some aspects, cadaver chondrocytes can comprise chondrocytes expressing other molecular markers such as a high molecular weight sulfated proteoglycan, such as, for example, chondroitin sulfate (Kato, Y., and Gospodarowicz, D., J. Cell Biol. 100: 477-485. 1985). Presence of such markers can be determined using materials and methods well known to skilled artisans, such as, for example, antibody detection and histological staining.

In some configurations, cadaver chondrocytes or cartilage, including cartilage tissue as well as cells, either directly extracted from a cadaver grown in vitro, can be harvested prior to implantation or injection into a patient using cell culture techniques and apparatuses well known to skilled artisans, such as culture methods for neocartilage described in U.S. Pat. Nos. 6,235,316 and 6,645,316 to Adkisson, and other general laboratory manuals on cell culture such as Sambrook, J. et al., Molecular Cloning: a Laboratory Manual (Third Edition), Cold Spring Harbor Laboratory Press, Cold Spring Harbor, N.Y., 2001; and Spector, D. L., et al., Culture and Biochemical Analysis of Cells, Cold Spring Harbor Laboratory Press, Cold Spring Harbor, N.Y. 1998. In vitro culture of cadaver chondrocytes can be used to increase numbers of chondrocytes which can be implanted into a patient. In addition, routine laboratory measures known to skilled artisans can be used to detect and remove non-chondrocyte cells from a cell culture, or to test a culture for the presence of biological contaminants such as microorganisms and viruses. Primary cultures established starting from cadaver chondrocytes can be grown as long as the chondrocytes remain viable and maintain their normal in vitro histological properties.

Various configurations of the present teachings include compositions comprising chondrocytes and one or more biocompatible molecules. These biocompatible molecules can include molecules that enhance survival an/or integration of implanted chondrocytes or cartilaginous tissues into an intervertebral disc. Examples of such molecules include, without limitation, fibrinogen, fibrin, thrombin, type I collagen, type II collagen, type III collagen, fibronectin, laminin, hyaluronic acid, hydrogel, pegylated hydrogel, chitosan, and combinations thereof. Various commercial formulations comprising such molecules, such as, for example, Tisseel® fibrin glue (Baxter Healthcare Corporation, Westlake Village, Calif.) can comprise a composition of the present teachings. Accordingly, a composition of the present teachings can comprise, in non-limiting example, chondrocytes grown in culture and Tisseel® fibrin glue.

In various methods of the present teachings, cadaver chondrocytes, including but not limited to cadaver chondrocytes grown in vitro and cartilage tissue maintained in tissue culture in vitro, can be implanted or injected into an intervertebral disc of a recipient patient using surgical methods and apparatuses known to skilled artisans but adapted for such use. In various configurations, chondrocytes or cartilage of the present teachings can be implanted or injected into an annulus of a degenerative intervertebral disc, a nucleus pulposus of an intervertebral disc, one or both endplates of a degenerative intervertebral disc, or a combination thereof. In certain aspects, an aperture can be introduced into the annulus of an intervertebral disc. The aperture can provide a path for introducing chondrocytes or cartilage tissue into a disc.

In various configurations, cells or tissue can be placed into an apparatus or device configured for transfer of chondrocytes to or from an intervertebral disc patient, such as, in non-limiting example a biopsy instrument or transplantation instrument comprising a hollow tube or needle, a syringe, a double syringe, a hollow tube, a hollow needle such as a Jamshidi needle, a Cook needle (Cook incorporated, Bloomington, Ind. USA), a cannula, a catheter, a trocar, a stylet, an obturator, or other instruments, needles or probes for cell or tissue injection, injection, or transfer known to skilled artisans. Accordingly, an apparatus of the present teachings can comprise cadaver chondrocytes as described above, as well as at least one hollow needle or tube through which the chondrocytes can be introduced into an intervertebral disc of a patient. In some configurations, the apparatus comprises a composition comprising the chondrocytes as well as at least one biocompatible molecule as described supra. These apparatuses can be configured for implanting or injecting chondrocytes into an annulus, a nucleus pulposus, and/or an endplate of a degenerative disc. Furthermore, surgical techniques such as vertebroplasty and kyphoplasty (Garfin, S. R., et al., Spine 26: 1511-1515, 2001) can be adapted for introduction of chondrocytes into a degenerative disc of a patient. In non-limiting example, an instrument for such as a bone tamp/balloon can be inserted into a degenerative intervertebral disc, and used to create or expand a space or cavity within a degenerative disc, for example in the nucleus pulposus of the disc. The balloon can be removed, and chondrocytes expressing type II collagen can then be injected into the expanded space, for example through a catheter.

In various embodiments and configurations, the present teachings also disclose methods of purveying to a treatment provider chondrocytes for repairing a degenerative intervertebral disc in a patient in need thereof. These methods can comprise obtaining chondrocytes from a cadaver, growing the chondrocytes in vitro, then delivering the chondrocytes to the treatment provider. The chondrocytes can be obtained from a cadaver using methods described supra, and can be chondrocytes which are adapted for injection into a degenerative intervertebral disc in a patient. The adaptation can comprise, in various configurations, expanding the numbers of chondrocytes through growth in vitro. Chondrocytes adapted for injection can also comprise, in certain aspects, chondrocytes which can be loosely connected or unattached to each other, and can be chondrocytes not comprised by cartilage tissue. The cadaver chondrocytes of these embodiments can be chondrocytes expressing type II collagen, as described supra, and can also be chondrocytes expressing high molecular weight sulfated proteoglycan, also as described supra. The chondrocytes can be delivered to a treatment provider, as either a chondrocytes grown in vitro and/or as cartilage tissue pieces as described supra. The treatment provider can be, in non-limiting example, a physician such as an orthopedic surgeon, or an agent or employee of the physician or a health care institution such as a hospital or outpatient clinic. Accordingly, in non-limiting example, cadaver chondrocytes can be grown in vitro, and delivered to the treatment provider via a delivery service such as, for example, a courier or an overnight shipper. Cadaver chondrocytes and/or cartilage tissue can be prepared for delivering by methods well known to skilled artisans. In some configurations, cadaver chondrocytes and/or cartilage tissue can be provided in a composition further comprising at least one biocompatible molecule as described supra. In alternative configurations, the chondrocytes and/or cartilage tissue can be packaged and sent separately from any biomolecule(s). The treatment provider can then form the composition by mixing the cells with the one or more biomolecules. In some aspects, the mixing can be done immediately prior to implanting the cells into a recipient patient.

EXAMPLE

The following example illustrates transplantation and survival of human chondrocytes transplanted into canine intervertebral disc tissue. In this example, a pilot animal study was conducted to determine whether human articular chondrocytes survive injection to produce cartilaginous matrices in experimental defects created in the intervertebral disk of adult canines. Gross morphologic and histological results obtained from this short-term pilot study (12 weeks) demonstrate that implanted chondrocytes can survive to produce cartilaginous matrices which integrate with surrounding host tissues.

Surgical Procedure: Prior to induction of anesthesia, six adult female dogs were sedated by the attending veterinarian or the veterinary technician/anesthetist using one of the following combinations: Atropine 0.05 mg/kg IM with or without Acepromizine 0.05-0.2 mg/kg IM. An 18 or 20 gauge 1¼ to 2 inch angio-catheter was placed in the cephalic saphenous or auricular vein for venous access. General anesthesia was induced with Pentothal (10-20 mg/kg IV to effect). Animals were intubated with a 7.0 mm-9.0 mm hi-low pressure cuff endotracheal tube. Anesthesia was maintained with isoflurane 2.5-4% in an air-oxygen mixture of 40-60%. The tube was connected to low-pressure continuous suction, and mechanical ventilation was initiated and maintained at 10 ml/kg tidal volume and at a rate of 8-10/minute. Crystalloids were provided at a rate of 7-10 mg/kg/hr.

Surgical exposure consisted of a 10 cm incision along the abdominal midline, followed by soft tissue dissection to permit transperitoneal exposure of the anterior lumbar spine.

Blunt dissection using a Cobb elevator and electrocautery was performed as needed to expose the anterior aspects of the L3-L4, L5-L6, and L7-S1 intervertebral disc space. Surgical defects (1×3 mm) were created through the annulus into the disc nucleus using a 16 gauge biopsy needle (Jamshidi needle) and aspiration. A significant volume of the nucleus was removed in concert with the annulus.

Human Neocartilage produced at ISTO Technologies according to U.S. Pat. Nos. 6,235,316 and 6,645,764 were enzymatically dissociated in HL-1 Serum-free Medium (Cambrex Bio Science, Walkersville, Md.) containing 60 units/ml CLS4 collagenase (Worthington, Lakewood, N.J.) and 50 units/mL hyaluronidase (Sigma, St. Louis, Mo.). The dissociated chondrocytes (derived from the articular cartilage of a six year old individual) were washed in fresh HL-1 medium and briefly exposed to 0.25% EDTA before pelleting at 500× g for 7 minutes. The cells were counted and stored in sterile cryovials until use. Chondrocyte viability was estimated to be greater than 90% by trypan blue exclusion. Six tubes were prepared each containing 2 million chondrocytes. The cells were then pelleted and the supernate removed. These samples were hand carried to the operating room on wet ice. Once defects were created, a chondrocyte suspension was prepared using 100 microliters of thrombin solution (Tisseel®), Baxter Healthcare Corporation, Westlake Village, Calif.). This step was completed immediately before mixing with an equivalent volume of the fibrin component (Tissee®) using the Tissee® injection device. 150-200 microliters of the cell suspension was injected into the intervertebral disk closest to the dog's tail (L7-S1 and L5-L6), whereas the highest vertebral level to be treated (L3-L4 or L4-L5) was filled with 100-150 microliters of cells or cell carrier. The cell suspension was injected at the base of the defect through a needle and withdrawn during expulsion until it began to spill out of the injection site, forming a solid gel. Two thirds of the control defects were left untreated (33%) or received fibrin carrier alone (33%). The final one-third of operated defects was treated with cells suspended in fibrin carrier as described above. Treatment at each of the levels was randomized to control for variability in disc size and location.

Following the surgical procedure, the fascia and underlying muscles were closed in an interrupted fashion using -0-Prolene and the skin approximated using Vicryl® (Ethicon, Inc. Somerville, N.J. USA) and Vetbond™ tissue adhesive (3M, St. Paul, Minn. USA). Blood loss, operative times and both intra- and peri-operative complications were recorded. Observations of ambulatory activities and wound healing were monitored daily, and all animals received analgesics after surgery.

Post-operative Care: After recovery from anesthesia, each dog was returned to its cage and housed singly for observation (daily) by veterinary technicians for any sign of adverse events related to surgery. Buprinorphine (0.01-0.02 mg/k IM or SC) was administered for relief of pain every 12 hours for the first 24 hours and prn thereafter. In general, the animals were pain free after 24 hrs.

Animal Harvest and Sample Collection: Dogs were sacrificed 12 weeks after surgery by overdose with euthanasia solution. Spines were removed, keeping the upper lumbar and sacral region intact. Musculoskeletal tissue was removed by dissection to expose the vertebral bodies for further sectioning using a band saw. Gross observation of the defects was performed using digital photography and the samples were immediately fixed in 10% neutral buffered formalin (Fisher Scientific, Fairlawn, N.J.) for 48 hrs. Samples were subsequently decalcified in 10% disodium EDTA (Sigma-Aldrich Co., St. Louis, Mo.) after four washes in PBS to remove formalin. Samples were then dehydrated in a graded alcohol series and processed using standard paraffin embedding.

Five micron sections were cut and stained with hematoxylin and eosin as well as safraninO for microscopic evaluation of the cartilaginous tissue present in control and operated intervertebral disks. Discs that were not exposed to the surgical procedures were used to establish normal histological features of the canine intervertebral disk.

Results: In general, the dogs handled the surgical procedure well, and all of the abdominal wounds healed rapidly without infection. There appeared to be no detrimental effect of multiple surgical procedures (operation at three vertebral levels in each animal) on the activity level of all dogs.

Figure 4:
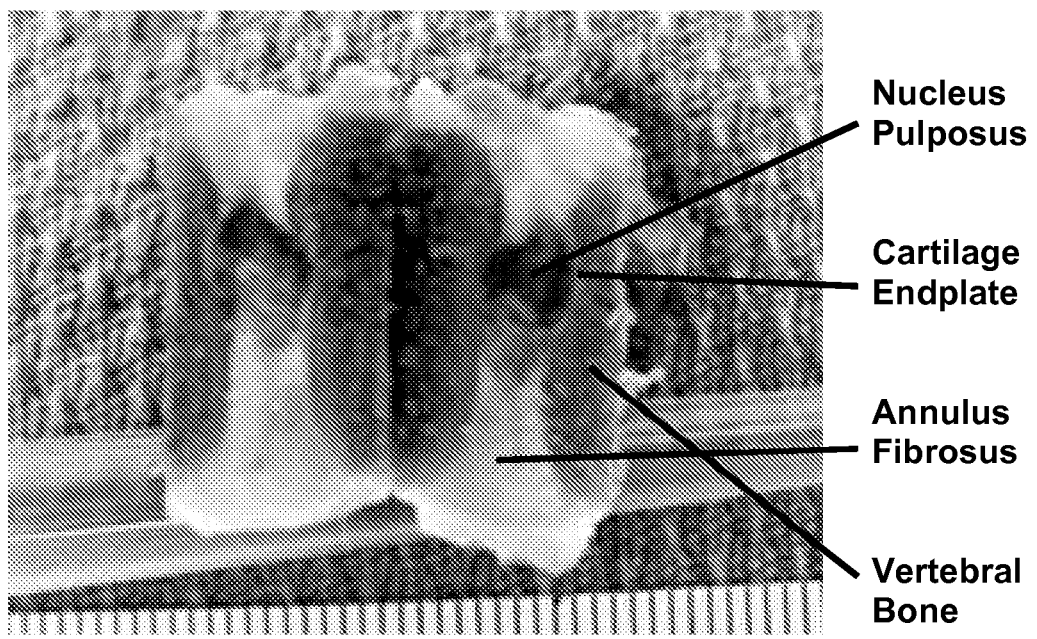
FIG. 4 illustrates the gross appearance of an intact unoperated disc harvested from the lumbar region of an adult canine.
Figure 5:
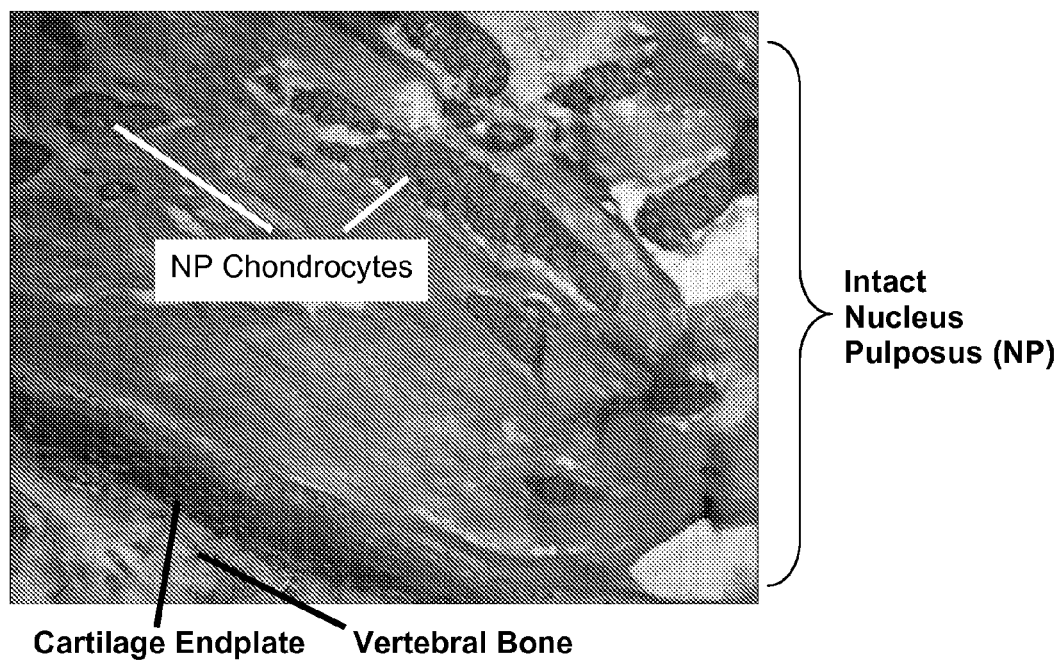
FIG. 5 illustrates an intact nucleus pulposus and the cartilaginous endplate of the disc shown in FIG. 4.

Gross macroscopic observation of the dissected vertebrae revealed normal disc structure in those discs that were not subjected to surgical intervention (FIG. 4). A glistening gelatinous center, corresponding to the nucleus pulposus, was identifiable in every case. Histological analysis revealed normal disc morphology in which the concentric rings of the annulus were observed to contain lower sulfated glycosaminoglycan content (fibrocartilaginous tissue) than the nucleus pulposus (NP) and the cartilage end plates (hyaline tissue), suggesting that surgical intervention at an adjacent level did not alter the morphological features of a disc that was not part of the procedure (FIG. 5).

Figure 6:
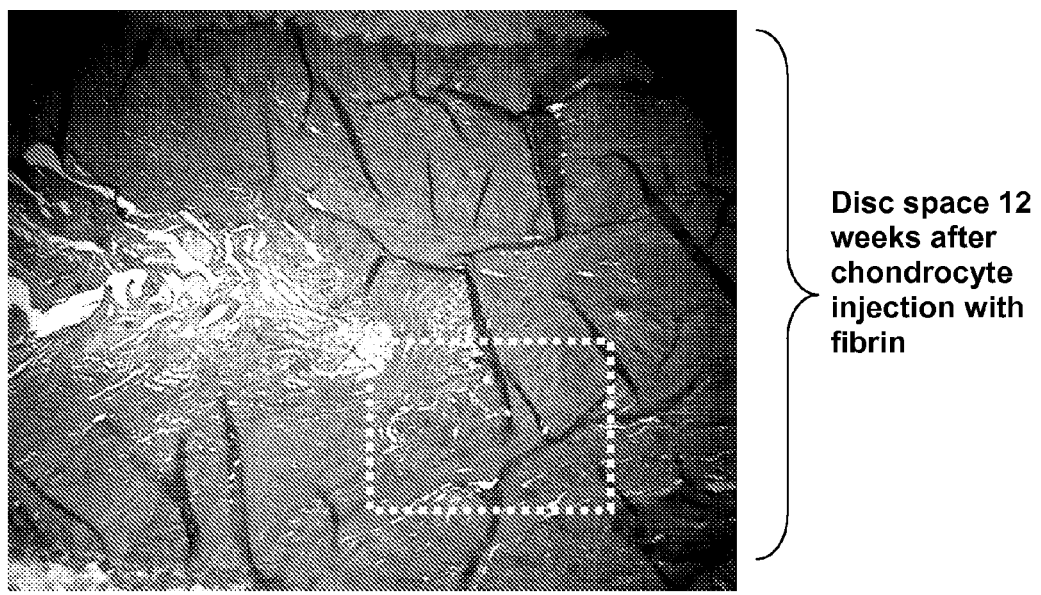
FIG. 6 illustrates a section of an intervertebral disk that was treated with human chondrocytes 12 weeks post-injection.

Those discs receiving neocartilage chondrocytes in fibrin glue were observed to contain viable chondrocytes in the disc space, and the injected chondrocytes had synthesized a hyaline matrix enriched in sulfated proteoglycan (FIGS. 6 and 7). Gross macroscopic observation of treated discs show viable cartilaginous tissue occupying the disc space (FIGS. 8A and B).

These results indicate that fibrin delivery to the disc space of chondrocytes derived from juvenile articular was successful and that the nature of newly synthesized tissue produced by the implanted chondrocytes appeared to be cartilaginous as determined by SafraninO staining. Most importantly, there was no histological evidence of lymphocytic infiltration into the operative site 12 weeks post-injection, suggesting that there was no immunologic rejection.

FIG. 4 illustrates the gross appearance of an intact unoperated disc harvested from the lumbar region of an adult canine. The disc is split in half to show the morphology of a normal intervertebral disk. The annulus fibrosus is the outer fibrocartilaginous structure surrounding the inner jelly-like structure or nucleus pulposus (NP). The cartilage endplate covers the surface of the upper and lower vertebral body.

FIG. 5 illustrates an intact nucleus pulposus and the cartilaginous endplate of the disc shown in FIG. 4. The section was stained with Safranin O to identify sulfated glycosaminoglycans in the NP and in the cartilage end plate. Notice that the NP chondrocytes are significantly larger than chondrocytes of the cartilage endplate and that the endplate contains greater levels of sulfated proteoglycan. Original magnification 100×

FIG. 6 illustrates a Safranin O-stained section of an intervertebral disk that was treated with human chondrocytes 12 weeks post-injection. The chondrocytes are viable and have synthesized a cartilaginous matrix that is highly enriched in sulfated glycosaminoglycans. The injected chondrocytes are much smaller than native NP chondrocytes identified in FIG. 5. The white square identifies the region shown in FIG. 7. Original magnification 40×.

Figure 7A:
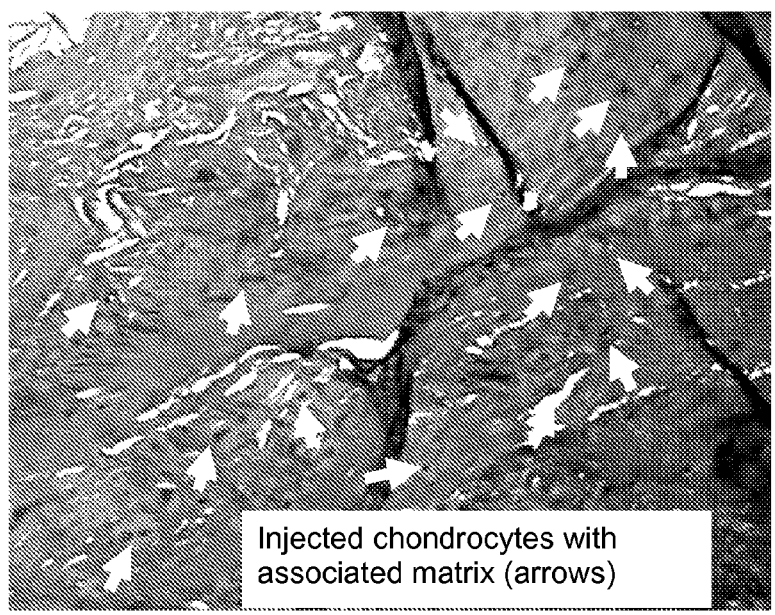
FIG. 7A represents the highlighted region of FIG. 6, illustrating the newly synthesized matrix that has replaced the native nucleus 12 weeks after chondrocyte injection.
Figure 7B:
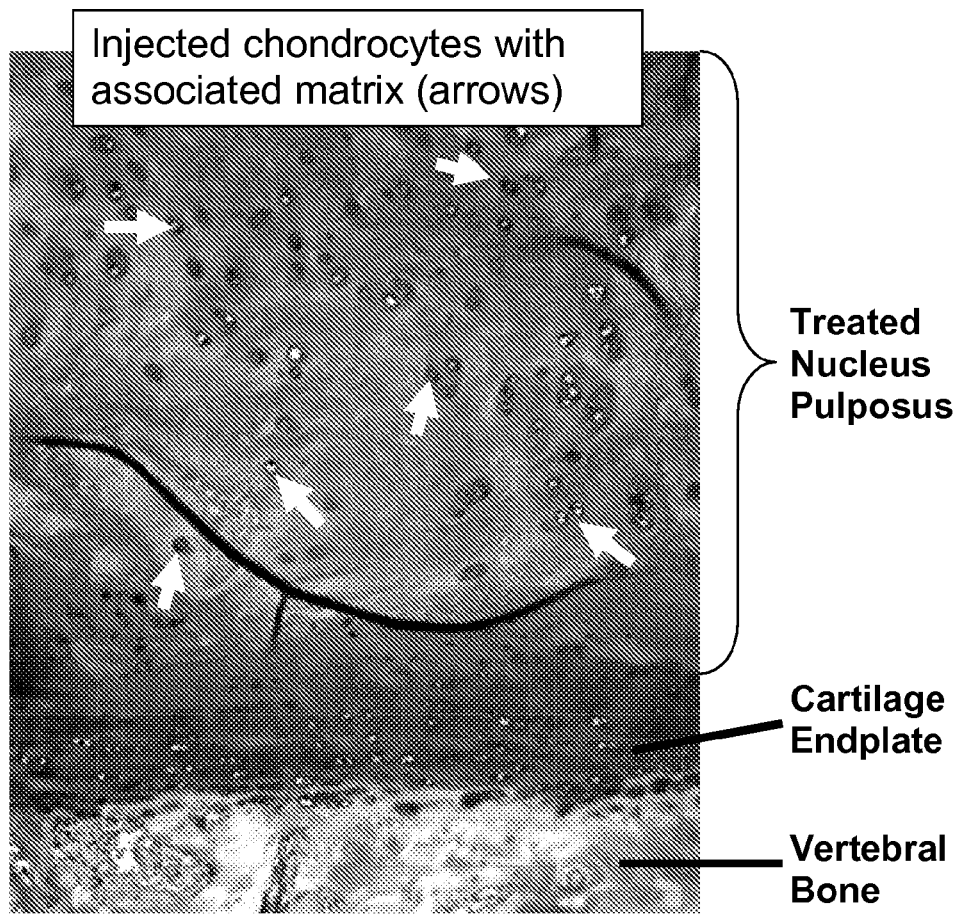
FIG. 7B is a histological image (100x) of a tissue section from the same study also showing newly synthesized matrix 12 weeks after chondrocyte injection into the disc nucleus.

FIG. 7A represents the highlighted region of FIG. 6, illustrating the newly synthesized matrix that has replaced the native nucleus 12 weeks after chondrocyte injection. The new matrix appears to be integrated well with the surrounding native tissues. Chondrocytes in this newly synthesized matrix (identified with white dotted circles) appear to be randomly distributed and of similar size to chondrocytes of the cartilaginous endplate. Original magnification 100.times. FIG. 7B more clearly illustrates the random distribution of viable chondrocytes identified in FIG. 7A and represents a tissue section from the same study, also taken 12 weeks after chondrocyte injection. FIG. 7B also shows chondrocytes (identified by arrows) well integrated with surrounding tissues, random distribution of chondrocytes and chondrocytes of similar size to chondrocytes of the cartilaginous endplate.

Figure 8:
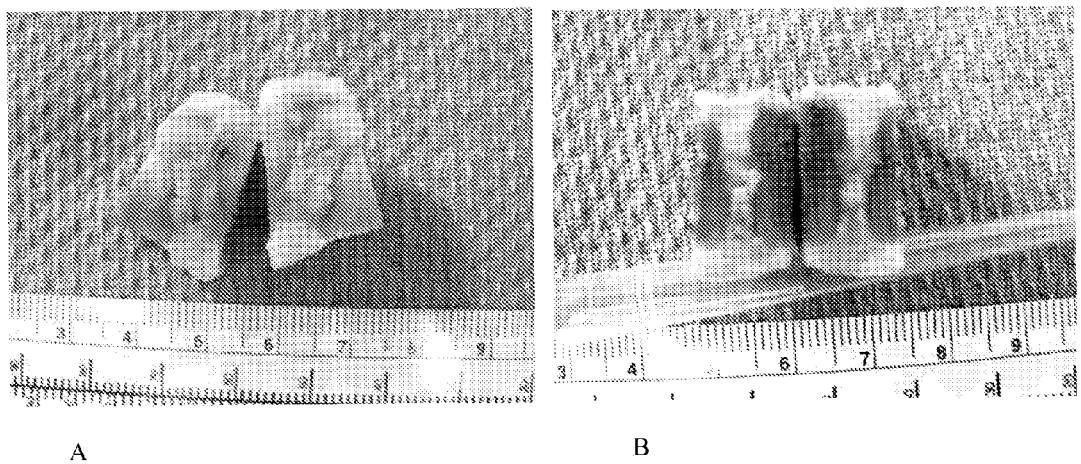
FIG. 8 illustrates the gross appearance of discs 12 weeks after chondrocyte injection.

FIG. 8 is in two parts. Panel A illustrates the gross appearance of a disc 12 weeks after chondrocyte injection. The native nucleus is no longer present and is replaced by newly synthesized cartilaginous tissue. Panel B illustrates the gross appearance of another disc treated in the same manner. The histological features of this disc are shown in FIGS. 6 and 7. The newly synthesized cartilaginous material produced after chondrocyte injection is expected to remodel and take on morphological features that are more characteristic of the native annulus and nucleus within 1 year after treatment.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

All publications, patents, patent applications and other references cited in this application are herein incorporated by reference in their entirety as if each individual publication, patent, patent application or other reference were specifically and individually indicated to be incorporated by reference.

What is claimed is:

1. A method of repairing a degenerative intervertebral disc in a human subject in need of such repair, the method comprising:
    (a) isolating a population of articular cartilage chondrocytes from a cadaver donor;
    (b) expanding said population in vitro in a substantially serum-free growth medium, thereby yielding expanded articular cartilage chondrocytes;
    (c) mixing said expanded articular cartilage chondrocytes with a thrombin solution to yield a mixture of expanded articular cartilage chondrocytes in thrombin;
    (d) adding fibrin to said mixture to yield a suspension of expanded articular cartilage chondrocytes; and then immediately
    (e) injecting said suspension into a degenerative intervertebral disc of a human subject.

2. The method of claim 1, wherein expanding the population of articular cartilage chondrocytes in vitro comprises expanding the articular cartilage chondrocytes at least 10 fold in vitro prior to injecting the suspension of expanded articular cartilage chondrocytes.

3. The method of claim 1, wherein injecting the suspension of expanded articular cartilage chondrocytes into the intervertebral disc comprises injecting the suspension of chondrocytes into the nucleus pulposus of the intervertebral disc.

4. The method of claim 1, further comprising extracting the viable articular chondrocytes from a cadaver no older than about 20 years of age at time of death.

5. The method of claim 1, further comprising extracting the population of articular cartilage chondrocytes from a cadaver donor deceased for at least about one hour at time of extraction.

6. The method of claim 1, further comprising forming an aperture in the annulus of the intervertebral disc.

7. The method of claim 1 wherein after injection, at least a portion of the injected articular cartilage chondrocytes produce an extracellular cartilaginous matrix that integrates with tissue of the disc.

* * * * *

UNITED STATES PATENT AND TRADEMARK OFFICE
CERTIFICATE OF CORRECTION

| | | |
|---|---|---|
| PATENT NO. | : 7,879,604 B2 | |
| APPLICATION NO. | : 11/063183 | |
| DATED | : February 1, 2011 | |
| INVENTOR(S) | : Mitchell S. Seyedin, Robert Spiro and H. Davis Adkisson, IV | |

It is certified that error appears in the above-identified patent and that said Letters Patent is hereby corrected as shown below:

Cover page in Title: "disk" should be --disc--

Cover page Assignee: "Technoliges" should be --Technologies--

At col. 1, Title: "disk" should be --disc--

At col. 5, line 28: "disk" should be --disc--

At col. 6, line 32: "disk" should be --disc--

At col. 8, line 54: "disk" should be --disc--

At col. 9, line 38: "disk" should be --disc--

At col. 10, line 15: "disk" should be --disc--

At col. 10, line 17: "disk" should be --disc--

At col. 10, line 53: "disk" should be --disc--

At col. 10, line 63: should be --.-- at end of line

At col. 11, line 13: ".times." should be --×--

Signed and Sealed this
Twenty-first Day of June, 2011

David J. Kappos
*Director of the United States Patent and Trademark Office*